US009341608B2

(12) United States Patent
Fish

(10) Patent No.: US 9,341,608 B2
(45) Date of Patent: May 17, 2016

(54) METHOD FOR DETERMINING EXPECTED SHELF LIFE OF SEAFOOD

(71) Applicant: Frank Fish, Woodland, WA (US)

(72) Inventor: Frank Fish, Woodland, WA (US)

( * ) Notice: Subject to any disclaimer, the term of this patent is extended or adjusted under 35 U.S.C. 154(b) by 0 days.

(21) Appl. No.: 14/684,617

(22) Filed: Apr. 13, 2015

(65) Prior Publication Data

US 2015/0293069 A1 Oct. 15, 2015

Related U.S. Application Data

(60) Provisional application No. 61/979,190, filed on Apr. 14, 2014.

(51) Int. Cl.
*G01N 33/12* (2006.01)
*G01N 21/78* (2006.01)
*G01N 21/29* (2006.01)
*G01N 33/00* (2006.01)

(52) U.S. Cl.
CPC .............. *G01N 33/12* (2013.01); *G01N 21/293* (2013.01); *G01N 21/783* (2013.01); *G01N 33/0054* (2013.01); *G01N 21/78* (2013.01); *Y10T 436/175383* (2015.01)

(58) Field of Classification Search
CPC ................. Y10T 436/17; Y10T 436/175383; G01N 21/25; G01N 21/29; G01N 21/293; G01N 21/77; G01N 21/78; G01N 21/783; G01N 21/80; G01N 33/0054; G01N 33/02; G01N 33/12
USPC ............. 436/20, 21, 106, 113, 147, 163, 164, 436/167, 169; 422/400, 420, 86, 87, 88
See application file for complete search history.

(56) References Cited

U.S. PATENT DOCUMENTS

| 2,606,102 | A |   | 8/1952 | Cook |
| 4,105,800 | A |   | 8/1978 | Jahns et al. |
| 5,482,726 | A | * | 1/1996 | Robinson, Jr. ........... A23B 4/00 426/238 |
| 5,653,941 | A |   | 8/1997 | Veretto et al. |
| 5,744,321 | A | * | 4/1998 | Harewood ............... C12Q 1/06 435/29 |
| 6,495,368 | B1 | * | 12/2002 | Wallach ............... G01N 31/221 422/421 |
| 7,014,816 | B2 | * | 3/2006 | Miller .................... G01N 31/22 422/421 |
| 7,033,839 | B1 | * | 4/2006 | Dobler .................. G01N 31/22 422/421 |
| 7,560,271 | B2 |   | 7/2009 | Leech et al. |

(Continued)

OTHER PUBLICATIONS

Byrne et al. Analyst, vol. 127, 2002, pp. 1338-1341.*

(Continued)

*Primary Examiner* — Maureen Wallenhorst
(74) *Attorney, Agent, or Firm* — Global Intellectual Property Agency, LLC

(57) ABSTRACT

A method of determining the expected shelf life of seafood. The method includes a step of placing a test strip against a piece of seafood, wherein the test strip includes an indicating pad having a pH indicator that is configured to change color in the presence of ammonia. The method further includes a step of ascertaining concentration on a parts per million level of ammonia by comparing the color of the pH indicator to a comparative chart, wherein the comparative chart includes a gradient of color intensity that indicates the concentration on a parts per million level of ammonia. Furthermore, the method includes a step of referencing a booklet having a plurality of charts to cross reference the concentration of ammonia detected by the test strip with the storage temperature to determine an expected shelf life for a piece of seafood.

1 Claim, 2 Drawing Sheets

(56) References Cited

U.S. PATENT DOCUMENTS

| | | |
|---|---|---|
| 8,257,980 B2 | 9/2012 | Schalkhammer |
| 2002/0151075 A1* | 10/2002 | Chen .................. G01N 31/221 436/20 |
| 2003/0003589 A1* | 1/2003 | Khalil .................. G01N 21/783 436/113 |
| 2005/0123439 A1 | 6/2005 | Patton et al. |
| 2005/0272157 A1* | 12/2005 | Liberman ................ C12Q 1/22 436/21 |
| 2006/0057022 A1* | 3/2006 | Williams ............... G01N 31/22 422/400 |

OTHER PUBLICATIONS

Pacquit et al. Talanta, vol. 69, 2006, pp. 515-520.*
Olafsdottir et al. International Journal of Food Microbiology, vol. 111, 2006, pp. 112-125.*

* cited by examiner

METHOD FOR DETERMINING EXPECTED SHELF LIFE OF SEAFOOD

CROSS REFERENCE TO RELATED APPLICATION

This application claims the benefit of U.S. Provisional Application No. 61/979,190 filed on Apr. 14, 2014. The above identified patent application is herein incorporated by reference in its entirety to provide continuity of disclosure.

FIELD OF THE INVENTION

The present invention relates to devices and methods for determining seafood freshness. Specifically, the present invention describes a method for determining expected shelf life for a piece of seafood, wherein the method utilizes a color changing test strip that changes color in the presence of ammonia. A color chart is provided for allowing the user to determine the concentration of ammonia and the freshness of the seafood

BACKGROUND OF THE INVENTION

Fish contain high quality protein and other essential nutrients making it an important part of a healthy diet. A variety of fish included in a well-balanced diet may contribute to overall heart health and aid in children's proper growth and development. However, it is important to handle seafood with care to reduce the risk of foodborne illness. Often, this is called food poisoning, which is often caused by consuming food contaminated with bacteria, viruses, parasites, or toxins. Symptoms can include diarrhea, nausea, vomiting, abdominal pain, malaise, and fever.

Often, the first preventive measure is to buy fresh fish that is refrigerated or displayed on a thick bed of fresh ice that is not melting. Generally, some indicators of freshness include: a fish should smell fresh and mild, not fishy, sour, or ammonia-like; a fish's eye should be clear and bulge a little; a fish should have firm shiny flesh and bright red gills free from milky slime; and the flesh should spring back when pressed. However, these indicators provide circumstantial evidence of a piece of seafood being past their prime. Therefore, there requires a need for a method that allows a user to accurately determine the freshness of a piece of seafood.

Devices and methods have been disclosed in the prior art that relate to testing for various compounds related to food spoilage. Test strips specifically for testing for ammonia are known in the prior art. However, the prior art does not provide a method that determines expected shelf life of seafood comprising a step of referencing a chart to cross reference the concentration of ammonia detected with the storage temperature to determine an expected shelf life.

The present invention provides a method of determining expected shelf life of seafood. The method comprises a step of placing a test strip against a piece of seafood, wherein the test strip includes an indicating pad having a pH indicator that is configured to responsively and discriminatingly change color in presence of contact with ammonia. The method further comprises a step of ascertaining concentration on a parts per million level of ammonia by comparing color of the pH indicator to a comparative chart, wherein the comparative chart includes a gradient of color intensity that substantially indicates the concentration of ammonia. Furthermore, the method comprises a step of referencing a booklet having a plurality of charts to cross reference the concentration of ammonia detected by the test strip with the storage temperature to determine an expected shelf life for a piece of seafood.

It is therefore submitted that the present invention is substantially divergent in design elements from the prior art, and consequently it is clear that there is a need in the art for an improvement to a method that allows a user to accurately determine the freshness of a piece of seafood. In this regard, the instant invention substantially fulfills these needs.

SUMMARY OF THE INVENTION

In view of the foregoing disadvantages inherent in the known types of seafood freshness determination methods now present in the prior art, the present invention provides a method for determining expected shelf life for a piece of seafood.

It is therefore an object of the invention to provide a new and improved method for determining expected shelf life of seafood that has all of the advantages of the prior art and none of the disadvantages.

Another object of the present invention is to provide a new and improved method for determining expected shelf life of seafood comprising a first step of placing a test strip against a piece of seafood.

Yet another object of the present invention is to provide a new and improved method for determining expected shelf life of seafood, wherein said test strip includes an indicating pad having an indicator that is configured to responsively and discriminatingly change color in the presence of ammonia.

Still yet another object of the present invention is to provide a new and improved method for determining expected shelf life of seafood further comprising a step of ascertaining concentration on a parts per million level of ammonia by comparing the color of said indicator to a comparative color chart.

A further object of the present invention is to provide a new and improved method for determining expected shelf life of seafood further comprising the step of determining storage temperature of the piece of seafood.

Yet a further object of the present invention is to provide a new and improved method for determining expected shelf life for seafood further comprising the step of referencing a booklet having a plurality of charts to cross reference the concentration of ammonia detected by said test strip with the storage temperature to determine an expected shelf life.

Other objects, features, and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
FIG. 1 shows an exemplary comparative chart for a pH indicator.

Reference is made herein to the attached drawings. Like reference numerals are used throughout the drawings to depict like or similar elements of the ammonia testing method. For the purposes of presenting a brief and clear description of the present invention, the preferred method will be discussed as used for determining expected shelf life for a piece of seafood. The figures are intended for representative purposes only and should not be considered to be limiting in any respect.

The ammonia testing method for seafood is configured to allow a user to determine an expected shelf life of a piece of seafood. The ammonia testing method for seafood comprises a first step of determining concentrations on a parts per million level of ammonia. Most preferably, this first step is performed using a test strip that is placed against a piece of seafood. The test strip includes a handle portion, an alkalizing pad, and an indicating pad. Preferably, the alkalizing pad is a soda lime pad used to adjust the pH of a confined test sample. The indicating pad is configured to provide the color change in a high pH environment. The indicating pad comprises a hydrophobic member with a coating.

Preferably, the hydrophobic member is porous and allows ammonia gas to pass through the member. When the gas passes through the membrane, it contacts indicator on the indicating pad and changes color. The change in color, if it occurs, is known therefor to selectively occur because of the presence of ammonia gas, which is the only gas that passes through that is responsive to the indicator. The color change can then be compared to a standard comparative chart. The chart comprises a gradient of colors, wherein the color corresponds to approximately a specific concentration of ammonia. The chart can be used to determine the concentration of ammonia in parts per million. In this way, the toxic ammonia potential risk can be at least semi quantitatively assessed as to whether it is safe (light yellow color), or at high risk (light green) or somewhere in between.

An indicator is configured to responsively and discriminatingly change color in the presence of ammonia. Depending upon the concentration of ammonia, gradients of color intensity can be achieved to indicate concentrations on a parts per million (ppm) level of ammonia. Suitable indicators include bromophenol blue, bromocresol green, sodium salt, and bromocresol purple as pH indicators.

Referring now to FIG. 1, there is shown a standard comparative chart. Typically, the standard comparative chart for a pH indicator includes a scale from 0.00 ppm to 6.00 ppm, wherein a safe level of 0.00 ppm is indicated by a light yellow color on the indicating pad. A yellow-green color, wherein the yellow is more dominant than the color indicates approximately 0.25 ppm. A green-yellow color, wherein the green is more dominant than the yellow indicates substantially around 0.50 ppm. A pale green color indicates substantially around 1.00 ppm. A less pale green color substantially indicates around 3.00 ppm. Finally, a light green color indicates substantially around 6.00 ppm. However, other pH indicators are alternatively used in other embodiments of this method, and these modifications are likewise contemplated. Furthermore, other scales indicating ammonia level are suitable, and likewise deemed within the scope of the present disclosure.

The hydrophobic membrane of the indicating pad is configured to detect the present of ammonia gas. Some hydrophobic membranes that would absorb pH indicators include, but are not limited to: Versapore-H (Pall-Gelman) (a hydrophilic acrylic copolymer with a hydrophobic surface treatment); PVDF (polyvinylidene fluoride) membranes; Fluorotrans (Pall-Gelman) Immobilon (Millipore) Nylon; Hydrolon (Pall-Gelman) PTFE-supported on polypropylene or polyester; Tetratex (BHA-Tex); and Polypropylene from CUNO. The hydrophobic membrane is configured to be fibrous and porous. Pore sizes for the membrane are available from a nominal 0.6 microns to 10 microns. Preferred pore size is from 0.2 microns to 2.5 microns, preferably 0.6 microns to 1.2 microns, and most preferably about 0.6 microns.

Furthermore, the ammonia testing method for seafood comprises a second step of determining the storage temperature of the tested seafood. The role of storage temperature on the spoilage rate of seafood is well known. Not only does storage temperature affect the rate of spoilage reaction, it also involves the growth of bacteria, such as *Pseudomonas fragi*, a common seafood spoilage bacterium. Bacteria are capable of optimally multiplying around 68° F. to 86° F., however, their growth can be restrained by keeping seafood at colder temperatures, which are also cold enough to prevent the growth of food-borne pathogens. Preferably, the metric of the storage temperature is in degrees Fahrenheit, however other suitable metrics are alternatively used.

Figure 2:
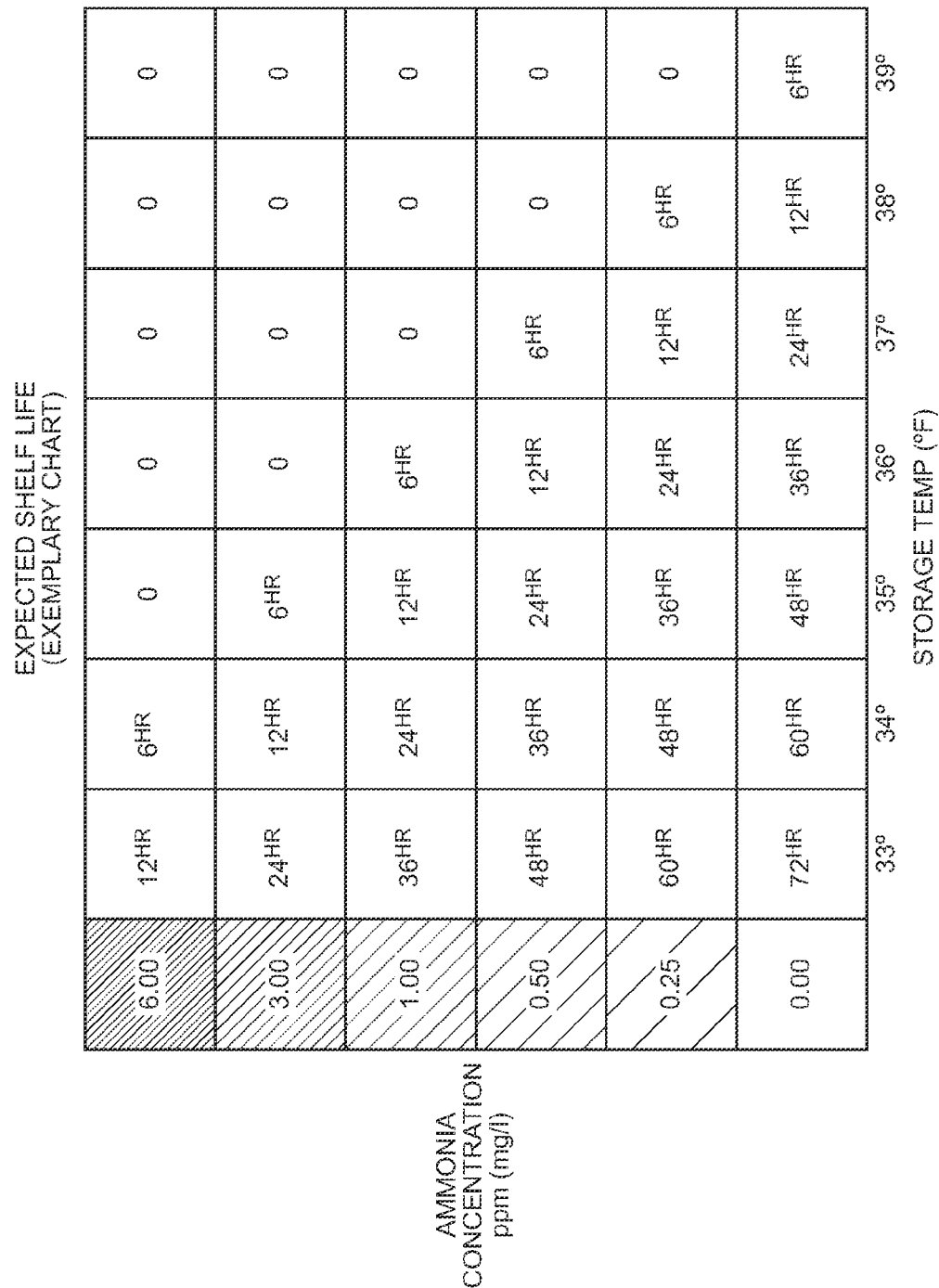
FIG. 2 shows an exemplary chart for determining shelf life of a piece of seafood.

Thereafter, the user references a booklet having a plurality of charts, such as the one illustrated in FIG. 2 that can be used to cross reference the level of ammonia detected by the test strip with the storage temperature to determine an expected shelf life post-examination. Each chart is applicable to a certain type of seafood, which allows a user to determine an expected shelf life for each type of seafood. Preferably, the expected shelf life is portrayed in hours, however, other metrics are also likewise contemplated.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of determining expected shelf life of seafood, comprising the steps of:
   placing a test strip against a piece of seafood;
   wherein said test strip is configured to change color in the presence of ammonia;
   comparing the color of said test strip to a comparative chart that indicates a concentration of ammonia corresponding to a particular color;
   wherein said comparative chart includes a gradient of color intensity that indicates said concentrations on a parts per million level of ammonia;
   determining storage temperature of said piece of seafood;
   referencing a booklet having a plurality of charts to cross reference the concentration of ammonia detected by said test strip with the storage temperature to determine an expected shelf life;

wherein each said chart is applicable to a certain type of seafood, which calculates an expected shelf life for each said type of seafood.

\* \* \* \* \*